United States Patent [19]

Rane et al.

[11] 4,431,816

[45] Feb. 14, 1984

[54] 2,3-DIHYDRO-2-(IMIDAZOLYLMETHYL) BENZO(B) THIOPHENES

[75] Inventors: Dinanath F. Rane, Emerson; John J. Wright, Cedar Grove; Russell E. Pike, Stanhope, all of N.J.

[73] Assignee: Schering Corporation, Kenilworth, N.J.

[21] Appl. No.: 354,463

[22] Filed: Mar. 3, 1982

Related U.S. Application Data

[63] Continuation-in-part of Ser. No. 215,948, Dec. 12, 1980, Pat. No. 4,352,808.

[30] Foreign Application Priority Data

Dec. 4, 1981 [EP] European Pat. Off. ........... 81110131

[51] Int. Cl.$^3$ .................. C07D 403/00; A01N 43/50; A01N 43/56
[52] U.S. Cl. ................................. 548/336; 424/273 R
[58] Field of Search ..................... 548/336; 424/273 R

[56] References Cited

U.S. PATENT DOCUMENTS 3,927,018 12/1975 Houlihan ............................. 548/336

FOREIGN PATENT DOCUMENTS 1445707 8/1973 United Kingdom ................ 548/336

Primary Examiner—Henry R. Jiles
Assistant Examiner—Robert C. Whittenbaugh
Attorney, Agent, or Firm—Anita W. Magatti; Bruce M. Eisen

[57] ABSTRACT

This invention relates to 2,3-dihydro-2-(imidazolylmethyl)benzo(b)thiophenes, to intermediates useful in their preparation, and to processes for preparing said intermediates. Also included in the invention are pharmaceutical compositions and the method of use of the compounds as antifungal agents.

1 Claim, No Drawings

2,3-DIHYDRO-2-(IMIDAZOLYLMETHYL)BENZO(B)THIOPHENES

This is a continuation-in-part of application Ser. No. 215,948, filed on Dec. 12, 1980 now U.S. Pat. No. 4,352,808.

This invention relates to 2,3-dihydro-2-(imidazolylmethyl)benzo(b)thiophenes represented by the formula

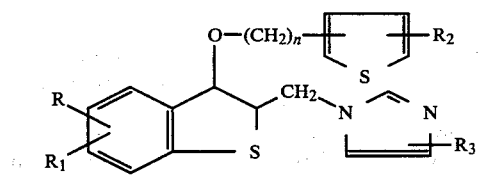

wherein:
n is 0 to 4;
R, $R_1$ and $R_2$ are independently hydrogen, lower alkyl groups, or halogen;
$R_3$ is hydrogen or lower alkyl;
and the pharmaceutically acceptable salts thereof.

As used in the specification and claims, the term "halogen" refers to fluorine, chlorine, bromine and iodine. "Lower alkyl" refers to hydrocarbon chains of 1 to 4 carbon atoms, for example methyl, ethyl, n-propyl, iso-propyl, or t-butyl groups.

The compounds of the invention are useful as antifungal agents.

This invention also relates to topical pharmaceutical compositions comprising compounds of formula I, to methods for their use in treating fungal infections, to intermediates useful in preparing compounds of formula I, and to a process for preparing said intermediates.

Of the compounds of formula I, preferred are those wherein n is 1. Also preferred are compounds of formula I wherein $R_3$ is hydrogen. A third group of preferred compounds is the cis isomers of compounds of formula I. A highly preferred embodiment of the invention is compounds of the cis isomer of formula I wherein n is 1 and $R_3$ is hydrogen, i.e. compounds of the following formula II:

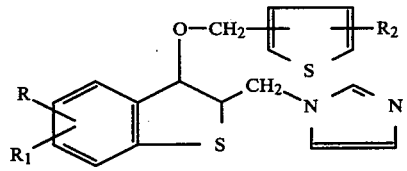

wherein R, $R_1$ and $R_2$ are independently hydrogen or halogen. Especially preferred are compounds of formula II wherein R and $R_1$ are independently hydrogen or halogen and $R_2$ is halogen. Of the halogens, chlorine and fluorine are most preferred.

Preferred compounds of formula II are:
cis-6-fluoro-3-(2'-chloro-3'-thenyloxy)-2,3-dihydro-2-(1''-imidazolylmethyl)benzo(b)thiophene,
cis-6-chloro-3-(2'-chloro-3'-thenyloxy)-2,3-dihydro-2-(1''-imidazolylmethyl)benzo(b)thiophene, and
cis-5-fluoro-3-(2'-chloro-3'-thenyloxy)-2,3-dihydro-2-(1''-imidazolylmethyl)benzo(b)thiophene.

Of these, the last is most preferred.

Compounds of formula I can exist in two isomeric forms, i.e. cis-2,3 or trans-2,3. Both forms are within the inventive concept as defined by formulae I and II, as are the individual optical isomers.

Also included within the composition-of-matter aspect of this invention are pharmaceutically acceptable salts of the compounds defined by formula I, e.g. acid addition salts. Such acid addition salts are made according to known procedures such as by neutralizing the free base with the appropriate acid, usually to about pH 5.

Suitable acids for this purpose include acids such as hydrochloric, sulfuric, phosphoric, hydrobromic, nitric and the like.

Compounds of this invention are prepared by reacting novel substituted hydroxyl compounds of the formula III:

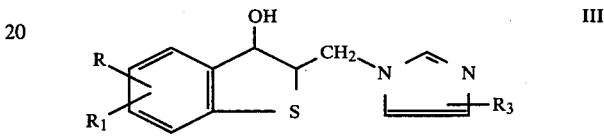

in which R, $R_1$ and $R_3$ are as defined for formula I, with an alkali metal base and with a halide $Z(CH_2)_nA$, in which Z is a thienyl group, n is as defined above, and A is a halogen atom, to give a compound of Formula I. If desired, the resulting compound is converted into a pharmaceutically acceptable acid addition salt.

The reaction of a compound of the general formula III with an alkali metal base (for example an alkali metal hydride, alkali metal hydroxide, alkali metal amide or alkali metal alcoholate) and with a halide, $Z(CH_2)_nA$, is carried out in an organic solvent, for example dimethylformamide, hexamethylphosphoric acid triamide, an aromatic hydrocarbon (e.g., benzene or toluene), an ether (e.g., diethyl ether, dioxane, tetrahydrofuran or ethylene glycol dimethyl ether), a lower alcohol, or a ketone (e.g., acetone) at a temperature within the range of 0°–100° C., and preferably within the range from 20°–60° C.

In order to increase the yield, the alkali metal base and the halide may be used in excess.

In a preferred method of preparation of compounds of Formula I such as disclosed in Example 1, sodium hydride is added to a solution of a hydroxyl compound of formula III in dimethylformamide at 0°–5° C., then allowed to react at room temperature for 1 hour, followed by the addition of the halide $Z(CH_2)_nA$ and reaction for another hour at room temperature. The compound of formula I thereby produced is isolated and purified utilizing known techniques such as extraction, chromatography, and recrystallization.

The halide starting materials, $Z(CH_2)_nA$, are generally known in the art or are made by procedures well known in the art. Typical halides useful in our procedure are 2-chloro-3-thenyl bromide, 2,5-dichloro-3-thenyl bromide, 2-chloro-5-thenyl bromide, and 3-thenyl bromide.

The starting materials of formula III may be made by the following novel process:
a thiochroman-4-one substituted in the benzene nucleus with R and $R_1$ functions as defined for formula III is first converted to the corresponding bromoketone by reaction with bromine in a solvent such as ether, chloroform, or carbon tetrachloride. The bromoketone thereby formed is then converted to the corresponding bromohydrin by reaction with a reducing agent, for example, sodium borohydride, in a solvent such as a lower alcohol. The resulting bromohydrin is reacted with imidazole or a substituted imidazole in a solvent such as dimethylformamide, hexamethylphosphoric acid triamide, a lower alcohol or acetonitrile to give a compound of formula III.

The present invention includes within its scope the method of eliciting an antifungal response in a host animal containing or subject to attack by fungi, which comprises subjecting said host animal to an antifungally effective amount of a 2,3-dihydro-2-(imidazolylmethyl)-benzo(b)thiophene of formula I.

The compounds of formula I exhibit antifungal activity against human and animal pathogens such as the following: Aspergillus, Candida, Epidermophyton, Geotrichum, Microsporum, Monosporium, Pityrosporum, Rhodotorula, Saccharomyces, Trichophyton, Trichosporon, and Torulopsis.

Additionally, compounds of formula I may exhibit antibacterial activity against human and animal pathogens such as the following: Actinomyces, Bacillus, Bacteriodes, Clostridium, Escherichia, Mycobacterium, Nocardia, Propionbacterium, Sarcina, Staphylococcus, Streptococcus, and Streptomyces. Compounds of formula I may also exhibit activity against such protozoal pathogens as Trichomonas.

The compounds of formula I also exhibit activity against fungi of primarily agricultural significance, such as the following: Cladosporium, Colletotrichum, Erysiphe, Fusarium, Helminthosporium, Penicillium, Peronospora, Phytophthora, Pithomyces, Polyspora, Puccina, Rhizoctonia, Sclerotium, Uromyces, and Venturia, and may show activity against bacteria of primarily agricultural significance, such as: Agrobacterium, Erwinia, and Xanthemonas.

As discussed hereinabove, the preferred compounds of this invention, i.e. those of formula II, are particularly valuable as antifungal agents as demonstrated by in vivo tests in animals, e.g. a hamster Candida infection model, a guinea pig dermatophyte infection model and a mouse systemic Candida infection model. These tests indicate the compounds of this invention to be broad-spectrum antifungal agents active against topical dermatophyte and vaginal and systemic yeast infections. Compounds of the present invention are generally preferred as topical antifungal agents, although they may also be active orally or parenterally.

In general, the dosage of compounds of formula I employed to combat a given fungal infection is similar to the dosage requirements of miconazole, clotrimazole, and ketoconazole, though the particular dosage level and the mode of administration will vary according to the particular host and the type and severity of the infection.

Also included in our inventive concept are pharmaceutical formulations comprising an antifungally effective amount of a compound of formula I in a pharmaceutically acceptable, non-toxic carrier for topical use.

Topical pharmaceutical dosage forms may be prepared according to procedures well known in the art, and may contain a variety of ingredients. The formulations for topical use include ointments, creams, lotions, powders, aerosols and sprays. Of these, ointments, lotions and creams may contain water, oils, fats, waxes, polyesters, alcohols, or polyols, plus such other ingredients as fragrances, emulsifiers and preservatives. Powders are made by mixing the active ingredient with a readily available, inert, pulverous distributing agent, such as talcum, calcium carbonate, tricalcium phosphate, or boric acid. Aqueous suspensions of the above powders may also be made. Solutions or emulsions may also be prepared using inert solvents which are preferably non-flammable, odorless, colorless, and non-toxic, for example vegetable oils, isopropanol, dimethyl sulfoxide, hydrogenated naphthalenes, and alkylated naphthalenes. Similarly, aerosol or non-aerosol sprays may be prepared using solutions or suspensions in appropriate solvents, e.g. difluorodichloromethane for aerosols.

In the case of topical formulations, e.g. ointments, creams, lotions, powders, or sprays, the formulation will contain about 0.1 to 3 grams of compound of formula I per 100 grams of carrier.

In addition to pharmaceutical uses, the compounds of this invention may also have industrial and agricultural applications in the control or prevention of fungi growth, e.g. as paint additives or medical equipment disenfectants.

The following example illustrates a typical formulation for topical antifungal use. The term "Drug" refers to cis-5-fluoro-3-(2'-chloro-3'-thenyloxy)-2,3-dihydro-2-(1''-imidazolylmethyl)benzo(b)thiophene, though it will be recognized that an equivalent amount of another compound of formula I may be substituted for the active ingredient.

| Cream | Amounts in (mg) | | |
|---|---|---|---|
| | A | B | C |
| Drug | 0.5 | 5.0 | 10.0 |
| Sorbitan Monostearate | 20.0 | 20.0 | 20.0 |
| Polysorbate 60 | 15.0 | 15.0 | 15.0 |
| Spermaceti Synthetic | 30.0 | 30.0 | 30.0 |
| Cetostearyl Alcohol | 100.0 | 100.0 | 100.0 |
| Octyl Dodecanol | 135.0 | 135.0 | 135.0 |
| Benzyl Alcohol | 10.0 | 10.0 | 10.0 |
| Purified Water | to make 1 gram | 1 gram | 1 gram |

PROCEDURE

Heat the sorbitan monostearate, 95% of the polysorbate 60, synthetic spermaceti, cetostearyl alcohol, and octyl dodecanol to 70° C. Dissolve the benzyl alcohol in 90% of the purified water heated to 75° C. Add the aqueous solution to the melted waxes and stir while cooling to 40° C. Dissolve the remaining portion of the polysorbate 60 in the remaining portion of water, add the drug and pass the slurry through a colloid mill. Add the slurry to the wax mixture and mix until cool.

The following Preparation and Example indicate the method used to prepare compounds represented by formula I.

PREPARATION 1

Cis-2,3-dihydro-3-hydroxy-2-(1'-imidazolylmethyl)-benzo(b)thiophenes (A)

Cis-6-Chloro-2,3-Dihydro-3-Hydroxy-2-(1'-Imidazolylmethyl)benzo(b)thiophene (1) 3-Bromo-7-Chlorothiochroman-4-One Dissolve 7-chlorothiochroman-4-one (10 gms., 50.3 mmols) in chloroform (100 ml.) and cool the solution to 0°-5° C. Add bromine (2.60 ml., 50.3 mmols) dropwise over a 10-minute period. Stir the reaction mixture at room temperature for one hour, then add chloroform (100 ml.) and extract with 10% aqueous sodium sulfite (100 ml.) followed by water (200 ml.). Dry the chloroform solution over anhydrous magnesium sulfate, filter and evaporate in vacuo to a residue. Recrystallize the residue from cyclohexane to give 3-bromo-7-chlorothiochroman-4-one, m.p. 109°–110° C.

(2) 3-Bromo-7-Chlorothiochroman-4-ol

Suspend 3-bromo-7-chlorothiochroman-4-one (59.6 gms., 215 mmols) in methanol (500 ml.), cool to 0.5° C., and with stirring add sodium borohydride (8.18 gms., 215 mmols) in three portions. Continue stirring the reaction mixture at room temperature for three hours, then pour into ice water (4 liters) and extract with chloroform (2 liters). Dry the chloroform solution over anhydrous magnesium sulfate, filter and evaporate in vacuo to a residue. Triturate the residue with chloroform/hexane to give 3-bromo-7-chlorothiochroman-4-ol, m.p. 141°–142° C.

(3) Cis-6-Chloro-2,3-Dihydro-3-Hydroxy-2-(1'-Imidazolylmethyl)benzo(b)thiophene

Add 3-bromo-7-chlorothiochroman-4-ol (5.27 gms., 18.8 mmols) and imidazole (12.8 gms., 188 mmols) to acetonitrile (100 ml.), and heat at reflux temperature for 4 hours. Pour the reaction mixture into water (500 ml.), and extract with chloroform (500 ml.). Wash the organic layer with water (500 ml.), dry the organic layer over anhydrous magnesium sulfate, filter and evaporate in vacuo. Triturate the resultant resultant residue with anhydrous ether, filter and recrystallize from acetonitrile to give cis-6-chloro-2,3-dihydro-3-hydroxy-2-(1'-imidazolylmethyl)benzo(b)thiophene.

(B)

In the procedure of above Preparation 1A(1–3), substitute for the starting compound, i.e. 7-chlorothiochroman-4-one, an equivalent quantity of each of the following:
(a) thiochroman-4-one,
(b) 6-chlorothiochroman-4-one,
(c) 8-chlorothiochroman-4-one,
(d) 5,7-dichlorothiochroman-4-one,
(e) 6,7-dichlorothiochroman-4-one,
(f) 6,8-dichlorothiochroman-4-one,
(g) 7-fluorothiochroman-4-one, and
(h) 6-fluorothiochroman-4-one,
to obtain respectively,
(a) cis-2,3-dihydro-3-hydroxy-2-(1'-imidazolylmethyl)benzo(b)thiophene,
(b) cis-5-chloro-2,3-dihydro-3-hydroxy-2-(1'-imidazolylmethyl)benzo(b)thiophene,
(c) cis-7-chloro-2,3-dihydro-3-hydroxy-2-(1'-imidazolylmethyl)benzo(b)thiophene,
(d) cis-4,6-dichloro-2,3-dihydro-3-hydroxy-2-(1'-imidazolylmethyl)benzo(b)thiophene,
(e) cis-5,6-dichloro-2,3-dihydro-3-hydroxy-2-(1'-imidazolylmethyl)benzo(b)thiophene,
(f) cis-5,7-dichloro-2,3-dihydro-3-hydroxy-2-(1'-imidazolylmethyl)benzo(b)thiophene,
(g) cis-6-fluoro-2,3-dihydro-3-hydroxy-2-(1'-imidazolylmethyl)benzo(b)thiophene, and
(h) cis-5-fluoro-2,3-dihydro-3-hydroxy-2-(1'-imidazolylmethyl)benzo(b)thiophene.

EXAMPLE 1

Cis-3-chlorothenyloxy-2,3-dihydro-2-(1'''-imidazolylmethyl)benzo(b)thiophenes

A.

Cis-6-Chloro-3-(2'-Chloro-3'-Thenyloxy)-2,3-Dihydro-2-(1''-Imidazolylmethyl)Benzo(b)Thiophene To a solution of cis-6-chloro-2,3dihydro-3-hydroxy2-(1''-imidazolylmethyl)benzo(b)thiophene (2.00 gms., 7.50 mmols) in dry dimethylformamide (20 ml.) cooled to 0°–5° C., add sodium hydride (50% dispersion, 0.40 gms., 8.25 mmols) and stir at room temperature for one hour. Add 2-chloro-3-thenyl bromide (1.75 gms., 8.25 mmols) and stir at room temperature for another hour. Pour the reaction mixture into ether (500 ml.) and extract with three 500 ml. portions of water. Dry the ether solution over anhydrous magnesium sulfate, filter and evaporate in vacuo. Chromatograph the resultant residue on silica gel eluting with chloroform. Combine the like eluates as determined by thin layer chromatography and evaporate in vacuo and recrystallize the resultant residue from cyclohexane to obtain cis-6-chloro-3-(2'-chloro-3'-thenyloxy)-2,3-dihydro-2-(1''-imidazolylmethyl)benzo(b)thiophene, m.p. 99°–101° C.

B.

Cis-6-Chloro-3-(2',5'-Dichloro-3'-Thenyloxy)-2,3-Dihydro-2-(1''-Imidazolylmethyl)Benzo(b)Thiophene In the procedure of Example 1A, substitute an equivalent quantity of 2,5-dichloro-3-thenyl bromide for 2-chloro-3-thenyl bromide to obtain the title compound.

C.

Treat each of the cis-2,3-dihydro-3-hydroxy-2-(1''-imidazolylmethyl)benzo(b)thiophenes prepared in Preparation 1B with 2-chloro-3-thenylbromide in a manner similar to that described in Example 1A to obtain, respectively,
(a) cis-3-(2'-chloro-3'-thenyloxy)-2,3-dihydro-2-(1''-imidazolylmethyl)benzo(b)thiophene,
(b) cis-5-chloro-3-(2'-chloro-3'-thenyloxy)-2,3-dihydro-2-(1''-imidazolylmethyl)benzo(b)thiophene,
(c) cis-7-chloro-3-(2'-chloro-3'-thenyloxy)-2,3-dihydro-2-(1''-imidazolylmethyl)benzo(b)thiophene,
(d) cis-4,6-dichloro-3-(2'-chloro-3'-thenyloxy)-2,3-dihydro-2-(1''-imidazolylmethyl)benzo(b)thiophene,
(e) cis-5,6-dichloro-3-(2'-chloro-3'-thenyloxy)-2,3-dihydro-2-(1''-imidazolylmethyl)benzo(b)thiophene,
(f) cis-5,7-dichloro-3-(2'-chloro-3'-thenyloxy)-2,3-dihydro-2-(1''-imidazolylmethyl)benzo(b)thiophene,
(g) cis-6-fluoro-3-(2'-chloro-3'thenyloxy)-2,3-dihydro-2-(1''-imidazolylmethyl)benzo(b)thiophene, and
(h) cis-5-fluoro-3-(2'-chloro-3'-thenyloxy)-2,3-dihydro-2-(1''-imidazolylmethyl)benzo(b)thiophene.

D.

Similarly, treat each of the cis-2,3-dihydro-3-hydroxy-2-(1''-imidazolylmethyl)benzo(b)thiophenes prepared in Preparation 1B with reagent used in Example 1B (2',5'-dichloro-3-thenyl bromide) to obtain respectively,
(a) cis-3-(2',5'-dichloro-3-thenyloxy)-2,3-dihydro-2-(1''-imidazolylmethyl)benzo(b)thiophene,
(b) cis-5-chloro-3-(2',5'-dichloro-3'-thenyloxy)-2,3-dihydro-(1''-imidazolylmethyl)benzo(b)thiophene,
(c) cis-7-chloro-3-(2',5'-dichloro-3'-thenyloxy)-2,3-dihydro-2-(1''-imidazolymethyl)benzo(b)thiophene, (d) cis-4,6-dichloro-3-(2',5'-dichloro-3'-thenyloxy)-2,3-dihydro-2-(1''-imidazolylmethyl)benzo(b)thiophene,
(e) cis-5,6-dichloro-3-(2',5'-dichloro-3'-thenyloxy)-2,3-dihydro-2-(1''-imidazolylmethyl)benzo(b)thiophene,
(f) cis-5,7-dichloro-3-(2',5'-dichloro-3'-thenyloxy)-2,3-dihydro-2-(1''-imidazolylmethyl)benzo(b)thiophene,
(g) cis-6-fluoro-3-(2',5'-dichloro-3'-thenyloxy)-2,3-dihydro-2-(1''-imidazolylmethyl)benzo(b)thiophene, and
(h) cis-5-fluoro-3-(2',5'-dichloro-3'-thenyloxy)-2,3-dihydro-2-(1''-imidazolylmethyl)benzo(b)thiophene.

EXAMPLE 2

Cis-6-chloro-3-(2'-chloro-5'-thenyloxy)-2,3-dihydro-2-(1''-imidazolylmethyl)benzo(b)thiophene In the procedure of Example 1A, substitute an equivalent amount of 2-chloro-5-thenyl bromide for 2-chloro-3-thenyl bromide to obtain the title compound, m.p. 94°–95° C.

EXAMPLE 3

Cis-3-(3'-thenyloxy)-2,3-dihydro-2-(1'-imidazolylmethyl)benzo(b)thiophenes

A.

In the procedure of Example 1A, substitute for 2-chloro-3-thenylbromide an equivalent quantity of 3-thenylbromide to obtain cis-6-chloro-3-(3'-thenyloxy)-2,3-dihydro-2-(1''-imidazolylmethyl)benzo(b)thiophene.

B.

In a similar manner, treat each of the cis-2,3-dihydro-3-hydroxy-2-(1'-imidazolylmethyl)benzo(b)thiophenes of Preparation 1B with 3-thenylbromide to obtain, respectively:
(a) cis-3-(3'-thenyloxy)-2,3-dihydro-2-(1''-imidazolylmethyl)benzo(b)thiophene,
(b) cis-5-chloro-3-(3'-thenyloxy)-2,3-dihydro-2-(1''-imidazolylmethyl)benzo(b)thiophene,
(c) cis-7-chloro-3-(3'-thenyloxy)-2,3-dihydro-2-(1''-imidazolylmethyl)benzo(b)thiophene,
(d) cis-4,6-dichloro-3-(3'-thenyloxy)-2,3-dihydro-2-(1''-imidazolylmethyl)benzo(b)thiophene,
(e) cis-5,6-dichloro-3-(3'-thenyloxy)-2,3-dihydro-2-(1''-imidazolylmethyl)benzo(b)thiophene,
(f) cis-5,7-dichloro-3-(3'-thenyloxy)-2,3-dihydro-2-(1''-imidazolylmethyl)benzo(b)thiophene,
(g) cis-6-fluoro-3-(3'-thenyloxy)-2,3-dihydro-2-(1''-imidazolylmethyl(benzo(b)thiophene, and
(h) cis-5-fluoro-3-(3'-thenyloxy)-2,3-dihydro-2-(1''-imidazolylmethyl)benzo(b)thiophene.

EXAMPLE 4

Cis-6-chloro-3-(2'-chloro-3'-thenyloxy)-2,3-dihydro-2-(1''-imidazolylmethyl)benzo(b)thiophene hydrochloride Dissolve cis-6-chloro-3-(2'-chloro-3'-thenyloxy)-2,3-dihydro-2-(1''-imidazolylmethyl)benzo(b)thiophene (2.0 gms.) in anhydrous ether (400 ml.). Add dropwise a saturated solution of HCl gas in 2-propanol until precipitation is complete, filter and dry the resultant residue to obtain the title compound.

The products of Examples 1B to D, 2 and 3 may be treated in a similar manner to obtain the corresponding hydrochloride acid addition salts.

In a similar manner, other compounds representative of formula I may be prepared, e.g.:
cis-6-chloro-3-(2'-chloro-3'-thenyloxy)-2,3-dihydro-2-[1''-(2'''-methylimidazolyl)methyl]benzo(b)thiophene,
cis-6-bromo-3-(2'-chloro-3'-thenyloxy)-2,3-dihydro-2-(1''-imidazolylmethyl)benzo(b)thiophene,
cis-5-fluoro-3-(2'-fluoro-3'-thenyloxy)-2,3-dihydro-2-(1''-imidazolylmethyl)benzo(b)thiophene,
cis-3-(2'-chloro-3'-thenyloxy)-2,3-dihydro-2-[1''-(2'''-methylimidazolyl)methyl]benzo(b)thiophene,
cis-5-methyl-3-(3'-thenyloxy)-2,3-dihydro-2-(1''-imidazolylmethyl)benzo(b)thiophene,
cis-5-fluoro-3-[(2'-chloro-3'-thienyl)ethoxy]-2,3-dihydro-2-(1''-imidazolylmethyl)benzo(b)thiophene, and
cis-3-[(3'-thienyl)propyloxy]-2,3-dihydro-2-(1''-imidazolylmethyl)benzo(b)thiophene.

We claim:
1. Compounds represented by the formula

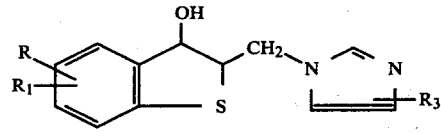

wherein
R and $R_1$ are independently hydrogen, lower alkyl groups, or halogen; and
$R_3$ is hydrogen or lower alkyl.

* * * * *